United States Patent [19]

Van Allan et al.

[11] 4,282,354

[45] Aug. 4, 1981

[54] ELECTROPHORETIC MIGRATION IMAGING PROCESS

[75] Inventors: James A. Van Allan; Louis J. Rossi, both of Rochester; Melvin S. Bloom, Penfield; Michael T. Regan, Fairport; Hal E. Wright; Joseph Y. Kaukeinen, both of Rochester, all of N.Y.

[73] Assignee: Eastman Kodak Company, Rochester, N.Y.

[21] Appl. No.: 30,973

[22] Filed: Apr. 18, 1979

Related U.S. Application Data

[60] Continuation-in-part of Ser. No. 889,715, Mar. 24, 1978, Pat. No. 4,165,984, which is a division of Ser. No. 804,042, Jun. 6, 1977, abandoned.

[51] Int. Cl.³ .............. C07D 407/10; C07D 333/76; C07C 121/62
[52] U.S. Cl. .............. 542/441; 260/465 H; 542/442; 542/443; 542/444; 542/445; 542/446; 542/447; 542/448; 542/449; 542/450; 542/451; 542/452; 542/432; 585/20; 585/21; 585/22; 585/23; 585/25; 585/26; 585/400; 549/43; 568/326; 568/328; 568/335
[58] Field of Search .............. 542/447, 448, 449, 445, 542/446, 444, 443, 442, 441, 450, 451, 452, 432; 260/465 H, 590 FA, 590 R, 592; 585/400, 25, 26, 23, 22, 21, 20; 549/43; 430/72, 71, 70

[56] References Cited

U.S. PATENT DOCUMENTS

| | | | |
|---|---|---|---|
| 3,336,357 | 8/1967 | Strobel et al. | 260/465 H |
| 3,915,702 | 10/1975 | Bergfjord et al. | 430/71 |
| 3,932,418 | 1/1976 | Janssens et al. | 542/450 |
| 3,987,060 | 10/1976 | Hashimoto | 549/43 |
| 3,992,203 | 11/1976 | Hörhold et al. | 430/70 |
| 4,072,519 | 2/1978 | Pearson | 430/72 |
| 4,122,114 | 10/1978 | Pearson | 260/465 H |
| 4,134,761 | 1/1979 | Okazaki | 542/449 |
| 4,184,871 | 1/1980 | Oba et al. | 430/70 |

OTHER PUBLICATIONS

Schönberg et al., Chem. Bericht. 106(1973), pp. 2663–2671.

Primary Examiner—Arthur P. Demers
Attorney, Agent, or Firm—Torger N. Dahl

[57] ABSTRACT

In general, materials having the structure

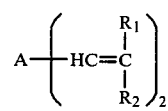

wherein
A represents phenylene, napthylene, anthracenediyl, and dibenzothien-diyl;
$R_1$ and $R_2$, which may be the same or different when taken alone represent hydrogen, cyano, alkylcarbonyl and arylcarbamoyl, arylcarbonyl, cyanoaryl;
$R_1$ and $R_2$, when taken together, represent sufficient atoms to form substituted and unsubstituted radicals selected from the group consisting of furanylidene, fluorenylidene, pyrimidinylidene, thiazolidinylidene, pyrrolinyl, and indenyl, isoxazolinylidene, pyrazolinylidene and indanylidene, wherein said substituents are selected from the group consisting of hydrogen, cyano, aryl, oxo, thioxo, nitro, alkyl, nitroaryl, carbamoyl and cyanoalkyl; and
alkyl represents an alkyl group having from one to six carbon atoms; aryl represents an aromatic nucleus selected from the group consisting of benzene, napthalene or anthracene, are useful in electrophoretic migration imaging processes.

2 Claims, 1 Drawing Figure

ELECTROPHORETIC MIGRATION IMAGING PROCESS

CROSS REFERENCE TO RELATED APPLICATIONS

This is a continuation-in-part of application Ser. No. 889,715 filed Mar. 24, 1978, now U.S. Pat. No. 4,165,984, which in turn is a division application of U.S. Ser. No. 804,042, filed June 6, 1977, now abandoned.

FIELD OF THE INVENTION

This invention relates to electrophoretic migration imaging processes and, in particular, to the use of certain novel photosensitive pigment materials in such processes.

BACKGROUND OF THE INVENTION

In the past, there has been extensive description in the patent and other technical literature of electrophoretic migration imaging processes. For example, a description of such processes may be found in U.S. Pat. Nos. 2,758,939 by Sugarman issued Aug. 14, 1956; 2,940,847, 3,100,426, 3,140,175 and 3,143,508, all by Kaprelian; 3,384,565, 3,384,488 and 3,615,558, all by Tulagin et al; 3,384,566 by Clark; and 3,383,993 by Yeh. In addition to the foregoing patent literature directed to conventional photoelectrophoretic migration imaging processes, another type of electrophoretic migration imaging process which advantageously provides for image reversal is described in Groner, U.S. Pat. No. 3,976,485 issued Aug. 24, 1976. This latter process has been termed photoimmobilized electrophoretic recording or PIER.

In general, each of the foregoing electrophoretic migration imaging processes typically employs a layer of electrostatic charge-bearing photoconductive particles, i.e., electrically photosensitive particles, positioned between two spaced electrodes, one of which may be transparent. To achieve image formation in these processes, the charge-bearing photosensitive particles positioned between the two spaced electrodes, as described above, are subjected to the influence of an electric field and exposed to activating radiation. As a result, the charge-bearing electrically photosensitive particles are caused to migrate electrophoretically to the surface of one or the other of the spaced electrodes, and one obtains an image pattern on the surface of these electrodes. Typically, a negative image is formed on one electrode, and a positive image is formed on the opposite electrode. Image discrimination occurs in the various electrophoretic migration imaging processes as a result of a net change in charge polarity of either the exposed electrically photosensitive particles (in the case of conventional electrophoretic migration imaging) or the unexposed electrically photosensitive particles (in the case of the electrophoretic migration imaging process described in the above-noted Groner patent application) so that the image formed on one electrode surface is composed ideally of electrically photosensitive particles of one charge polarity, either negative or positive polarity, and the image formed on the opposite polarity electrode surface is composed ideally of electrically photosensitive particles having the opposite charge polarity, either positive or negative.

In any case, regardless of the particular electrophoretic migration imaging process employed, it is apparent that an essential component of any such process is the electrically photosensitive particles. And, of course, to obtain an easy-to-read, visible image it is important that these electrically photosensitive particles be colored, as well as electrically photosensitive. Accordingly, as is apparent from the technical literature regarding electrophoretic migration imaging processes, work has been carried on in the past and is continuing to find particles which possess both useful levels of electrical photosensitivity and which exhibit good colorant properties. Thus, for example, various types of electrically photosensitive materials are disclosed for use in electrophoretic migration imaging processes, for example, in U.S. Pat. Nos. 2,758,939 by Sugarman, 2,940,847 by Kaprelian, and 3,384,488 and 3,615,558 by Tulagin et al., noted hereinabove.

In large part, the art, to date, has generally selected useful electrically photosensitive or photoconductive pigment materials for electrophoretic migration imaging from known classes of photoconductive materials which may be employed in conventional photoconductive materials which may be employed in conventional photoconductive elements, e.g., photoconductive plates, drums, or webs used in electrophotographic office-copier devices. For example, both Sugarman and Kaprelian in the above-referenced patents state that electrically photosensitive materials useful in electrophoretic migration imaging processes may be selected from known classes of photoconductive materials. And, the phthalocyanine pigments described as a useful electrically photosensitive material for electrophoretic imaging processes in U.S. Pat. No. 3,615,558 by Tulagin et al. have long been known to exhibit useful photoconductive properties.

SUMMARY OF THE INVENTION

In accord with the present invention, a group of materials has been discovered which are useful in electrophoretic migration imaging processes. With one exception, these materials are novel over the prior art known to applicants. None have been previously identified as photoconductors. Said materials have the following structure:

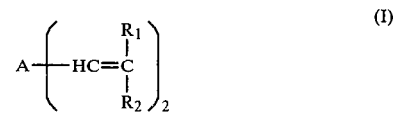

wherein
A represents phenylene, naphthylene, anthracenediyl, and dibenzothien-diyl;
$R_1$ and $R_2$, which may be the same or different when taken alone represent hydrogen, cyano, alkylsulfonyl, alkylcarbonyl and arylcarbamoyl, cyanoaryl, arylcarbonyl, and hydrogen;
$R_1$ and $R_2$, when taken together, represent sufficient atoms to form substituted and unsubstituted radicals selected from the group consisting of furanylidene, fluorenylidene, pyrimidinylidene, thiazolidinylidene, pyrrolinyl, indenyl, isoxazolinylidene, pyrazolinylidene, indanyliden carboxy-indene and dithiolyl, wherein said substituents are selected from the group consisting of hydrogen, cyano, aryl, oxo, thiooxo, nitro, alkyl, nitroaryl, carbamoyl, and cyanoalkyl, except that when:
$R^1$ is hydrogen, $R^2$ must be other than hydrogen.

Aryl, as a suffix or prefix, is defined herein to mean an aromatic nucleus such as benzene, napthalene and anthracene. Eunctional equivalents of both A above and Aryl may be used and both A and Aryl can have non-interfering substituents. Alkyl, as a prefix or suffix, is defined herein to mean alkyl radicals having from 1 to about 6 carbon atoms.

When used in an electrophoretic migration imaging process, charge-bearing, electrically photosensitive particles formulated from the materials of the present invention are positioned between two spaced electrodes; preferably these particles are contained in an electrically insulating carrier such as an electrically insulating liquid or an electrically insulating, liquefiable matrix material, e.g., a thixotropic or a heat- and/or solvent-softenable material, which is positioned between the spaced electrodes. While so positioned between the spaced electrodes, the photosensitive particles are subjected to an electric field and exposed to a pattern of activating radiation. As a consequence, the charge-bearing, electrically photosensitive particles undergo a radiation-induced variation in their charge polarity and migrate to one or the other of the electrode surfaces to form on at least one of these electrodes an image pattern representing a positive-sense or negative-sense image of the original radiation exposure pattern.

DESCRIPTION OF THE PREFERRED EMBODIMENTS

Figure 1:
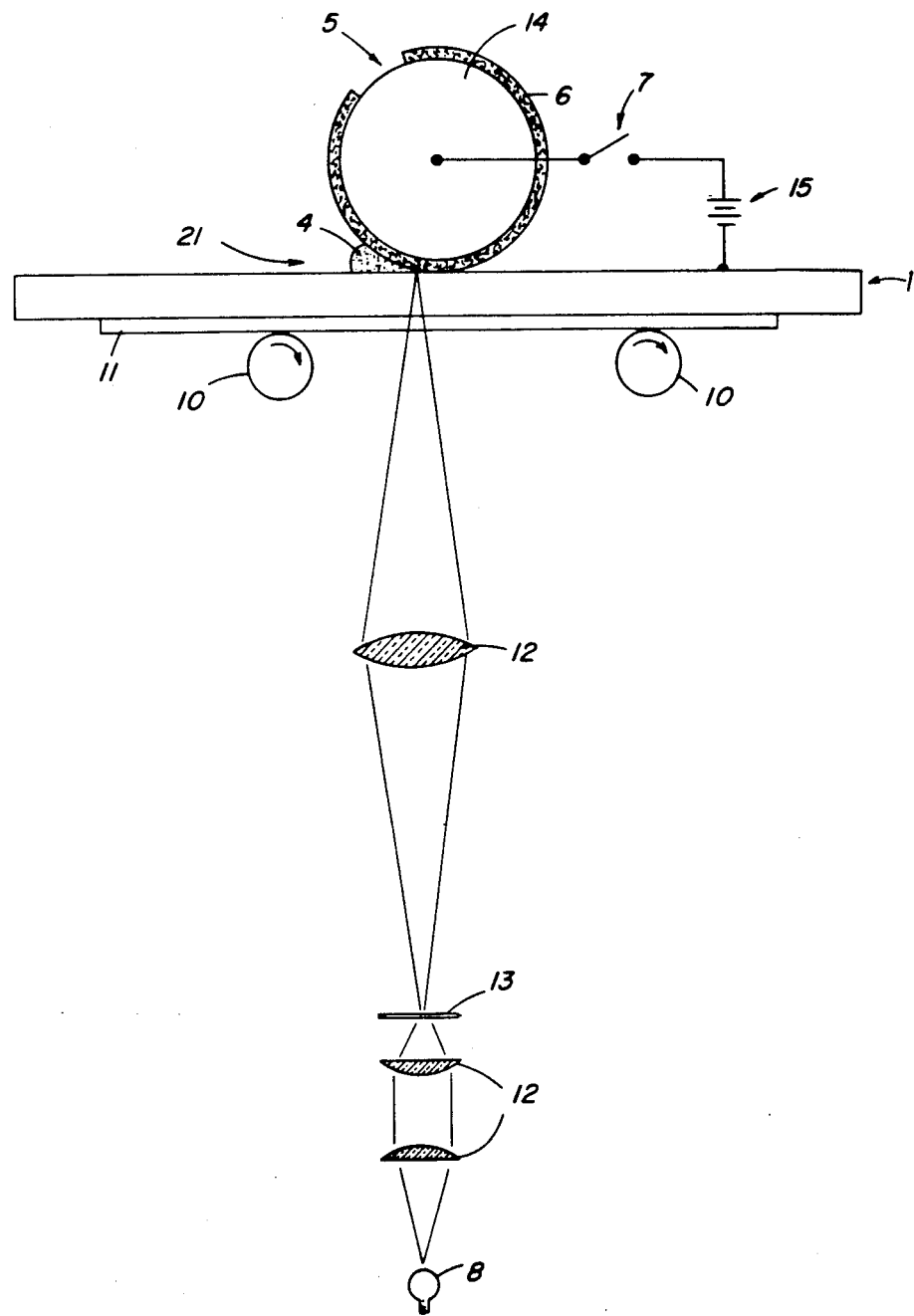
FIG. 1 represents diagrammatically a typical imaging apparatus for carrying out the electrophoretic migration imaging process of the invention.

In accordance with one embodiment of the present invention there is provided a group of novel colorant materials which are useful in electrophoretic migration imaging processes. These materials have the formula:

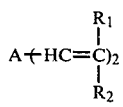

(II)

wherein

A represents phenylene, naphthylene, anthracenediyl and dibenzothien-diyl;

$R_1$ and $R_2$, which may be the same or different when taken alone represent hydrogen, cyano, and cyanoaryl, arylcarbonyl, hydrogen;

$R_1$ and $R_2$, when taken together, represent sufficient atoms to form substituted and unsubstituted radicals selected from the group consisting of furanylidene, fluorenylidene, pyrimidinylidene, thiazolidinylidene, pyrrolinyl, indenyl, isoxazolinylidene, pyrazolinylidene, indanylidene and dithiolyl, wherein said substituents are selected from the group consisting of hydrogen, cyano, aryl, oxo, thiooxo, nitro, alkyl, nitroaryl, carbamoyl, and cyanoalkyl, except that when: $R_1$ is hydrogen, $R_2$ must be other than hydrogen.

In accordance with another embodiment of the present invention, there is provided an electrophoretic migration imaging process which comprises subjecting an electrically photosensitive colorant material positioned between two electrodes to an applied electric field and exposing said material to an image pattern of radiation to which the material is photosensitive, thereby obtaining image formation on at least one of said electrodes, the improvement which comprises using as at least a portion of said material an electrically photosensitive colorant material according to Formula I.

In accordance with another embodiment of the present invention there is provided a group of materials which are especially useful in electrophoretic migration imaging processes. Such especially useful materials have a structure according to general Formula I wherein A represents naphthylene, anthracenediyl or benzothiophen-diyl;

$R_1$ and $R_2$, are both cyano or when taken together provide sufficient atoms to form a substituted or unsubstituted furanylidene radical and said substituents are selected from the group consisting of cyano, phenyl, nitrophenyl and oxo.

In addition to the useful levels of electrophotosensitivity exhibited by the materials of Formula I above in electrophoretic migration imaging processes, the materials of Formula I generally exhibit certain other properties which make these materials quite useful in electrophoretic migration imaging processes. The materials of Formula I are typically highly colored materials, generally exhibiting an absorption maximum to visible light at a wavelength greater than 410 nm, preferably in the 420 to 600 nm region of the visible spectrum.

In general, the photosensitive materials of Formula I above which have, to date, been found most useful in the present invention because of their high degree of photosensitivity tend to exhibit a maximum absorption wavelength, λmax, within the range of from about 420 to about 600 nm. A variety of different materials within the class defined by Formula I has been tested and found to exhibit useful levels of electrical photosensitivity in electrophoretic migration imaging processes. A partial listing of representative such materials is included herein in Table I.

TABLE I

| Material: |
|---|
| 1. 5,5'-(9,10-anthracenediyldimethylidyne)bis[3-cyano-4-phenyl-(5H)-furan-2-one] |
| 2. 5,5'-(9,10-anthracenediyldimethylidyne)bis[3,4-di-(p-nitrophenyl)-(5H)-furan-2-one] |
| 3. 9,10-bis(dicyanoethenyl)anthracene |

TABLE I-continued

Material:

4. 5,5'-(9,10-anthracenediyldimethylidyne)bis(1,3-diethyl-1,3,5-trihydro-pyrimidine-2,4,6-trione)

5. 2,2'-(9,10-anthracenediyldimethylidyne)bis(indan-1,3-dione)

6. 5,5'-(9,10-anthracenediyldimethylidyne)bis(N-ethyl-2-thioxo-thiazolidin-4-one)

7. 5,5'-(9,10-anthracenediyldimethylidyne)bis(3-carbamoyl-4-phenyl-furan-2-one)

8. 4,4'-(9,10-anthracenediyldimethylidyne)bis(3-phenyl-isoxazolin-5-one)

9. 5,5'-(9,10-anthracenediyldimethylidyne)bis(2-thioxo-thiazolidin-4-one)

10. 4,4'-(1,4-phenylenedimethylidyne)bis(3-carbamoyl-1-phenyl pyrazolin-5-one)

11. 1,1'-(1,4-phenylenedimethylidyne)bis(3-carboxy-indene)

12. 2,6-bis(dicyanoethenyl)naphthalene 13. 5,5'-(2,6-naphthalenediyldimethylidyne)bis(3-cyano-4-phenyl-furan-2-one)

14. 2,6-bis[β-cyano-β-(p-cyanophenyl)ethenyl]naphthalene 15. 5,5'-(dibenzothien-2,8-diyldimethylidyne)bis(3-cyano-4-phenyl-furan-2-one)

16. 5,5'-(dibenzothien-2,8-diyldimethylidyne)bis[3,4-di(p-nitrophenyl)-furan-2-one]

17. 5,5'-(dibenzothien-2,8-diyldimethylidyne)bis(3-carbamoyl-4-phenyl-furan-2-one)

The materials described by general Formula I are prepared by the same general procedures. Illustrative of such procedures is the preparation of 5,5'-(9,10-anthracenediyldimethylidyne)bis[3,4-di(p-nitrophenyl)-furan-2-one] as follows.

A solution of 1.17 g (5.0 m mole) of 9,10-anthracenedicarboxaldehyde, 3.26 g (10.0 m mole) of 3,4-di-p-nitrophenyl-2(5H)furanone, 0.5 ml of piperidine and 0.5 ml of acetic acid in 100 ml of toluene was refluxed with stirring for two hours with about 0.2 ml of water azeotropically collected in a Dean Stark trap. A bright red solid separated at reflux, the mixture was cooled and the solid collected to give 3.9 g of the material having a m.p. greater than 400° C.

Calcd for $C_{48}H_{26}N_4O_{12}$ (850.8): C, 67.7; H, 3.09; N, 6.59. Found: C, 67.1; H, 3.1; N, 6.3.

As indicated hereinabove, the electrically photosensitive material described herein is useful in the preparation of the electrically photosensitive imaging particles used in electrophoretic migration imaging processes. In general, electrically photosensitive particles useful in such processes have an average particle size within the range of from about 0.01 micron to about 20 microns, preferably from about 0.01 to about 5 microns. Typically, these particles are composed of one or more colorant materials such as the colorant materials described in the present invention. However, these electrically photosensitive particles may also contain various non-photosensitive materials such as electrically insulating polymers, charge control agents, various organic and inorganic fillers, as well as various additional dyes or pigment materials to change or enhance various colorant and physical properties of the electrically photosensitive particle. In addition, such electrically photosensitive particles may contain other photosensitive materials such as various sensitizing dyes and/or chemical sensitizers to alter or enhance their response characteristics to activating radiation.

When used in an electrophoretic migration imaging process in accord with the present invention, the electrically photosensitive materials described by Formula I hereinabove, are typically positioned in particulate form, between two or more spaced electrodes, one or both of which typically being transparent to radiation to which the electrically photosensitive material is light-sensitive, i.e., activating radiation. Although the electrically photosensitive material, in particulate form, may be dispersed simply as a dry powder between two spaced electrodes and then subjected to a typical electrophoretic migration imaging operation such as that described in U.S. Pat. No. 2,758,939 by Sugarman, it is more typical to disperse the electrically photosensitive particulate material in an electrically insulating carrier, such as an electrically insulating liquid, or an electrically insulating, liquefiable matrix material, such as a heat- and/or solvent-softenable polymeric material or a thixotropic polymeric material. Typically, when one employs such a dispersion of electrically photosensitive particulate material and electrically insulating carrier material between the spaced electrodes of an electrophoretic migration imaging system, it is conventional to employ from about 0.05 part to about 2.0 parts of electrically photosensitive particulate material for each 10 parts by weight of electrically insulating carrier material.

As indicated above, when the electrically photosensitive particles used in the present invention are dispersed in an electrically insulating carrier material, such carrier material may assume a variety of physical forms and may be selected from a variety of different materials. For example, the carrier material may be a matrix of an electrically insulating, normally solid polymeric material capable of being softened or liquefied upon application of heat, solvent, and/or pressure so that the electrically photosensitive particulate material dispersed therein can migrate through the matrix. In another, more typical embodiment of the invention, the carrier material can comprise an electrically insulating liquid such as decane, paraffin, Sohio Oderless Solvent 3440 (a kerosene fraction marketed by the Standard Oil Company, Ohio) various isoparaffinic hydrocarbon liquids such as those sold under the trademark Isopar G by Exxon Corporation and having a boiling point in the range of 145° C. to 186° C., various halogenated hydrocarbons such as carbon tetrachloride, trichloromonofluoromethane, and the like, various alkylated aromatic hydrocarbon liquids such as the alkylated benzenes, for example, xylenes, and other alkylated aromatic hydrocarbons such as are described in U.S. Pat. No. 2,899,335. An example of one such useful alkylated aromatic hydrocarbon liquid which is commerically available in Solvesso 100 made by Exxon Corporation. Solvesso 100 has a boiling point in the range of about 157° C. to about 177° C. and is composed of 9 percent dialkyl benzene, 37 percent trialkyl benzenes, and 4 percent aliphatics. Typically, whether solid or liquid at normal room temperatures, i.e., about 22° C., the electrically insulating carrier material used in the present invention is a material having a resistivity greater than about $10^9$ ohm-cm, preferably greater than about $10^{12}$ ohm-cm. When the electrically photosensitive particles formed from the materials of the present invention are incorporated in a carrier material, such as one of the above-described electrically insulating liquids, various other addenda may also be incorporated in the resultant imaging suspension. For example, various charge control agents may be incorporated in such a suspension to improve the uniformity of charge polarity of the electrically photosensitive particles dispersed in the liquid suspension. Such charge control agents are well known in the field of liquid electrographic developer compositions where they are employed for purposes substantially similar to that described herein. Thus, extensive discussion of the materials herein is deemed unnecessary. These materials are typically polymeric materials incorporated by admixture thereof into the liquid carrier vehicle of the suspension. In addition to, and possibly related to, the aforementioned enhancement of uniform charge polarity, it has been found that the charge control agents often provide more stable suspensions, i.e., suspensions which exhibit substantially less settling out of the dispersed photosensitive particles.

In addition to the foregoing charge control agent materials, various polymeric binder materials such as various natural, semi-synthetic or synthetic resins, may be dispersed or dissolved in the electrically insulating carrier to serve as a fixing material for the final photosensitive particle image formed on one of the spaced electrodes used in electrophoretic migration imaging systems. Here again, the use of such fixing addenda is conventional and well known in the closely related art of liquid electrographic developer compositions so that extended discussion thereof is unnecessary herein.

The process of the present invention will be described in more detail with reference to the accompanying drawing, FIG. 1, which illustrates a typical apparatus which employs the electrophoretic migration imaging process of the invention.

FIG. 1 shows a transparent electrode 1 supported by two rubber drive rollers 10 capable of imparting a translating motion to electrode 1 in the direction of the arrow. Electrode 1 may be composed of a layer of optically transparent material, such as glass or an electrically insulating, transparent polymeric support such as poly(ethylene terephthalate), covered with a thin, optically transparent, conductive layer such as tin oxide, indium oxide, nickel, and the like. Optionally, depending upon the particular type of electrophoretic migration imaging process desired, the surface of electrode 1 may bear a "dark charge exchange" material, such as a solid solution of an electrically insulating polymer and 2,4,7-trinitro-9-fluorenone as described by Groner in U.S. Pat. No. 3,976,485 issued Aug. 24, 1976.

Spaced opposite electrode 1 and in pressure contact therewith is a second electrode 5, an idler roller which serves as a counter electrode to electrode 1 for producing the electric field used in the electrophoretic migration imaging process. Typically, electrode 5 has on the surface thereof a thin, electrically insulating layer 6. Electrode 5 is connected to one side of the power source 15 by switch 17. The opposite side of the power source 15 is connected to electrode 1 so that as an exposure takes place, switch 7 is closed and an electric field is applied to the electrically photosensitive particulate material 4 which is positioned between electrodes 1 and 5. Typically electrically photosensitive particulate material 4 is dispersed in an electrically insulating carrier material such as described hereinabove.

The electrically photosensitive particulate material 4 may be positioned between electrodes 1 and 5 by applying material 4 to either or both of the surfaces of electrodes 1 and 5 prior to the imaging process by by injecting electrically photosensitive imaging material 4 between electrodes 1 and 5 during the photophoretic migration imaging process.

As shown in FIG. 1, exposure of electrically photosensitive particulate material 4 takes place by use of an exposure system consisting of light source 8, an original image 11 to be reproduced, such as a photographic transparency, a lens system 12, and any necessary or desirable radiation filters 13, such as color filters, whereby electrically photosensitive material 4 is irradiated with a pattern of activating radiation corresponding to original image 11. Although the electrophoretic migration imaging system represented in FIG. 1 shows electrode 1 to be transparent to activating radiation from light source 8, it is possible to irradiate electrically photosensitive particulate material 4 in the nip 21 between electrodes 1 and 5 without either of electrodes 1 or 5 being transparent. In such a system, although not shown in FIG. 1, the exposure source 8 and lens system 12 is arranged so that image material 4 is exposed in the nip or gap 21 between electrodes 1 and 5.

As shown in FIG. 1, electrode 5 is a roller electrode having a conductive core 14 connected to power source 15. The core is in turn covered with a layer of insulating material 6, for example, baryta paper. Insulating material 6 serves to prevent or at least substantially reduce the capability of electrically photosensitive particulate material 4 to undergo a radiation induced charge alteration upon interaction with electrode 5. Hence, the term "blocking electrode" may be used, as is conventional in the art of electrophoretic migration imaging, to refer to electrode 5.

Although electrode 5 is shown as a roller electrode and electrode 1 is shown as essentially a translatable, flat plate electrode in FIG. 1, either or both of these electrodes may assume a variety of different shapes such as a web electrode, rotating drum electrode, plate electrode, and the like as is well known in the field of electrophoretic migration imaging. In general, during a typical electrophoretic migration imaging process wherein electrically photosensitive material 4 is dispersed in an electrically insulating, liquid carrier, electrodes 1 and 5 are spaced such that they are in pressure contact or very close to one another during the electrophoretic migration imaging process, e.g., less than 50 microns apart. However, where electrically photosensitive particulate material 4 is dispersed simply in an air gap between electrodes 1 and 5 or in a carrier such as a layer of heat-softenable or other liquefiable material coated as a separate layer on electrode 1 and/or 5, these electrodes may be spaced more than 50 microns apart during the imaging process.

The strength of the electric field imposed between electrodes 1 and 5 during the electrophoretic migration imaging process of the present invention may vary considerably; however, it has generally been found that optimum image density and resolution are obtained by increasing the field strength to as high a level as possible without causing electrical breakdown of the carrier medium in the electrode gap. For example, when electrically insulating liquids such as isoparaffinic hydrocarbons are used as the carrier in the imaging apparatus of FIG. 1, the applied voltage across electrodes 1 and 5 typically is within the range of from about 100 volts to about 4 kilovolts or higher.

As explained hereinabove, image formation occurs in electrophoretic migration imaging processes as the result of the combined action of activating radiation and electric field on the electrically photosensitive particulate material 4 disposed between electrodes 1 and 5 in the attached drawing. Typically, for best results, field application and exposure to activating radiation occur concurrently. However, as would be expected, by appropriate selection of various process parameters such as field strength, activating radiation intensity, incorporation of suitable light sensitive addenda in or together with the electrically photosensitive particles formed from the material of Formula I, e.g., by incorporation of a persistent photoconductive material, and the like, it is possible to alter the timing of the exposure and field application events so that one may use sequential exposure and field application events rather than concurrent field application and exposure events.

When disposed between imaging electrodes 1 and 5 of FIG. 1, electrically photosensitive particulate material 4 exhibits an electrostatic charge polarity, either as a result of triboelectric interaction of the particles or as a result of the particles interacting with the carrier material in which they are dispersed, for example, an electrically insulating liquid, such as occurs in conventional liquid electrographic developing compositions composed of toner particles which acquire a charge upon being dispersed in an electrically insulating carrier liquid.

Image discrimination occurs in the electrophoretic migration imaging process of the present invention as a result of the combined application of electric field and activating radiation on the electrically photosensitive particulate material dispersed between electrodes 1 and 5 of the apparatus shown in FIG. 1. That is, in a typical imaging operation, upon application of an electric field between electrodes 1 and 5, the particles 4 of charge-bearing, electrically photosensitive material are attracted in the dark to either electrodes 1 or 5, depending upon which of these electrodes has a polarity opposite to that of the original charge polarity acquired by the electrically photosensitive particles. And, upon exposing aprticles 4 to activating electromagnetic radiation, it is theorized that there occurs neutralization or reversal of the charge polarity associated with either the exposed or unexposed particles. In typical electrophoretic migration imaging systems wherein electrode 1 bears a conductive surface, the exposed, electrically photosensitive particles 4, upon coming into electrical contact with such conductive surface, undergo an alteration (usually a reversal) of their original charge polarity as a result of the combined application of electric field and activating radiation. Alternatively, in the case of photoimmobilized electrophoretic recording (PIER), wherein the surface of electrode 1 bears a dark charge exchange material as described by Groner in aforementioned U.S. Pat. No. 3,976,485, one obtains reversal of the charge polarity of the unexposed particles, while maintaining the original charge polarity of the exposed electrically photosensitive particles, as these particles come into electrical contact with the dark charge exchange surface of electrode 1. In any case, upon the application of electric field and activating radiation to electrically photosensitive particulate material 4 disposed between electrodes 1 and 5 of the apparatus shown in FIG. 1, one can effectively obtain image discrimination so that an image pattern is formed by the electrically photosensitive particles which corresponds to the original pattern of activating radiation. Typically, using the apparatus shown in FIG. 1, one obtains a visible image on the surface of electrode 1 and a complementary image pattern on the surface of electrode 5.

Subsequent to the application of the electric field and exposure to activating radiation, the images which are formed on the surface of electrodes 1 and/or 5 of the apparatus shown in FIG. 1 may be temporarily or permanently fixed to these electrodes or may be transferred to a final image receiving element. Fixing of the final particle image can be effected by various techniques, for example, by applying a resinous coating over the surface of the image bearing substrate. For example, if electrically photosensitive particles 4 are dispersed in a liquid carrier between electrodes 1 and 5, one may fix the image or images formed on the surface of electrode 1 and/or 5 by incorporating a polymeric binder material in the carrier liquid. Many such binders (which are well known for use in liquid electrophotographic liquid developers) are known to acquire a charge polarity upon being admixed in a carrier liquid and therefore will, themselves, electrophoretically migrate to the surface of one or the other of the electrodes. Alternatively, a coating of a resinous binder (which has been admixed in the carrier liquid), may be formed on the surfaces of electrodes 1 and/or 5 upon evaporation of the liquid carrier.

The electrically photosensitive colorant material of Formula I may be used to form monochrome images, or the material may be admixed with other electrically photosensitive material of proper color and photosensitivity and used to form polychrome images. Said electrically photosensitive colorant material of the present invention also may be used as a sensitizer for other electrophotosensitive material in the formation of monochrome images. When admixed with other electrically photosensitive materials, selectively the photosensitive material of the present invention may act as a sensitizer and/or as an electrically photosensitive particle. Many of the electrically photosensitive colorant materials having Formula I have especially useful hues which make them particularly suited for use in polychrome imaging processes which employ a mixture of two or more differently colored electrically photosensitive particles. When such a mixture of multicolored electrically photosensitive particles is formed, for example, in an electrically insulating carrier liquid, this liquid mixture of particulate material exhibits a black coloration. Preferably, the specific cyan, magenta, and yellow particles selected for use in such a polychrome imaging process are chosen so that their spectral response curves do not appreciably overlap whereby color separation and subtractive multicolor image reproduction can be achieved.

The following examples illustrate the utility of the Formula I materials in electrophoretic migration imaging processes.

EXAMPLES

Imaging Apparatus

An imaging apparatus was used in each of the succeeding examples to carry out the electrophoretic migration imaging process described herein, including the photoimmobilized electrophoretic recording (PIER) process described by Groner in U.S. Pat. No. 3,976,485 and photoelectrophoresis (PEP). This apparatus was a device of the type illustrated in FIG. 1. In this apparatus, a translating film based having a conductive coating served as electrode 1 and was in pressure contact with a 10 centimeter diameter aluminum roller 14 covered with dielectric paper coated with poly(vinyl butyral) resin which served as electrode 5. Plate 1 was supported by two 2.8 cm. diameter rubber drive rollers 10 positioned beneath film plate 1 such that a 2.5 cm. opening, symmetric with the axis of the aluminum roller 14, existed to allow exposure of electrically photosensitive particles 4 to activating radiation. The original transparency 11 to be reproduced was taped to the back side of film plate 1.

The original transparency to be reproduced consisted of adjacent strips of clear, red, green and blue filters. The light source consisted of a Kodak Carousel Projector 860H with a 300 watt ELH Lamp and a 6.8 cm. f/3.5 lens. The light was modulated with a Kodak No. 5 eleven step 0.3 neutral density step tablet. The residence time in the action of 0.25 cm and a translational velocity of 25 cm/second (for PIER: 0.25 cm and a translational velocity of 1 inch/second) zone was 10 milliseconds (PIER 100 milliseconds). Exposure expressed as the log of the light intensity (Log I) in the nip was as follows:

|  | Filters | Log I erg/cm$^2$/sec. | |
|---|---|---|---|
|  |  | PEP | PIER |
| *W0 | Clear | 4.70 | 4.46 |
| *W29 | Red | 4.09 | 3.84 |
| *W99 | Green | 3.24 | 3.00 |
| *W47B | Blue | 3.04 | 2.76 |

*WRATTEN FILTER NUMBERS

The voltage between the electrode 5 and film plate 1 was about 2 kv. Film plate 1 was negative polarity in the case where electrically photosensitive particulate material 4 carried a positive electrostatic charge, and film plate 1 was positive in the case where electrically photosensitive electrostatically charged particles were negatively charged. The translational speed of film plate 1 was about 25 cm. per second. In the following examples, image formation occurs on the surfaces of film plate 1 and electrode 5 after simultaneous application of light exposure and electric field to electrically photosensitive material evaluated for use as electrically photosensitive particulate material 4 was admixed with a liquid carrier as described below to form a liquid imaging dispersion which was placed in nip 21 between the electrodes 1 and 5. If the material being evaluated for use as material 4 possessed a useful level of electrical photosensitivity in an electrophoretic, suspension one obtained a negative-appearing image reproduction of original 11 on electrode 5 and a complementary image on electrode 1. When the above described apparatus was used to form images according to the aforementioned photoimmobilized electrophoretic recording process (PIER) described in U.S. Pat. No. 3,976,485, electrode 1 was overcoated with a 6 micron thick dark charge exchange layer consisting of 38% 2,4,7-trinitro-9-fluorenone in Lexan 145 polycarbonate. The speed of electrode 1 in this case was about 2.5 cm/second.

Imaging Dispersion Preparation

Imaging dispersions were prepared to evaluate each of the material in Table I. The dispersions were prepared by first making a stock solution of the following components. The stock solution was prepared simply by combining the components:

| PEP | | PIER | |
|---|---|---|---|
| Isopar G | 2.2 g | Isopar G | 2.5 g |
| Solvesso 100 (Exxon Corp.) | 1.3 g | Piccotex 100 | 2.5 g |
| Piccotex 100 (Penn. Industrial Chem. Corp.) | 1.4 g | | |
| *PVT | 0.1 g | | |

*PVT is poly(vinyltoluene-co-laurylmethacrylate-co-lithium methacrylate-co-methacrylic acid) 56/40/3.6/0.4

A 5 g. aliquot of the stock solution was combined in a closed container with 0.045 g. of the Table I material to be tested and 12 g. of Pioneer 440 stainless steel balls. The preparation was then milled for three hours on a paint shaker.

EXAMPLES 1–3

Materials 1, 2 and 3 from Table 1 were evaluated in a photoelectrophoretic (PEP) and in the PIER process. In each case images were obtained which exhibited that materials 1, 2 and 3 possessed useful levels, electrophotosensitivity. Dmax and Dmin data were presented in Tables II–IV.

The relative sensitivity measurements reported in Example 1 are relative reciprocal electrical sensitivity measurements. The relative reciprocal electrical sensitivity measures the speed of a given material relative to other material typically within the same test group of elements. The relative reciprocal sensitivity values are not absolute sensitivity values. However, relative reciprocal sensitivity values are related to absolute sensitivity values. The relative reciprocal electrical sensitivity is a dimensionless number and is obtained simply by arbitrarily assigning a value, Ro, to one particular reciprocal absolute sensitivity of one particular photoconductive control element. The relative reciprocal sensitivity Rn, of any other photoconductive element, n, relative to this value, Ro, may then be calculated as follows:

$$Rn = (a_n)(R_o/A_o)$$

wherein An is the absolute reciprocal electrical sensitivity in ($cm^2$/ergs) of n, Ro is the sensitivity value arbitrarily assigned to the control element, and Ao is the absolute reciprocal electrical sensitivity measured in ($cm^2$/ergs) of the control element.

TABLE II

Example 1
Material 1 from Table I

| DISPERSION | CHARGE EXCHANGE ELECTRODES | RELATIVE SENSITIVITY | |
|---|---|---|---|
| | | $\Delta D = 0.1$ | $\Delta D = (D_{MAX} - D_{MIN})/2$ |
| PEP | 0.1 OD Cermet (Cr . SiO) Evaporated on polyethylene terephthalate | CLEAR 1.00* RED — GREEN — BLUE — | 0.74 — — — |
| PEP | 0.1 OD Cermet (Cr . SiO) Evaporated on polyethylene terephthalate | CLEAR 3.63 RED — GREEN 7.07 BLUE — | 1.04 — 2.40 — |
| PEP | PIER | CLEAR 2.14 RED — GREEN 2.51 BLUE — | 0.98 — — — |
| PEP | PIER | CLEAR 9.53 RED — GREEN 19.23 BLUE — | 1.70 — 4.07 — |
| PEP | 0.4 OD Nickelized polyethylene terephthalate | CLEAR 1.23 RED — GREEN 1.35 BLUE — | 0.73 — — — |
| PIER | PIER | CLEAR — RED — GREEN — BLUE — | — — — — |

*Arbitrarily assigned a relative value of 1.00.

TABLE III

Example 2
Material 2 from Table I

| DISPERSION | CHARGE EXCHANGE ELECTRODES | $D_{MAX}$ | $D_{MIN}$ |
|---|---|---|---|
| PEP | 0.1 OD Cermet (Cr . SiO) Evaporated on polyethylene terephthalate | 0.61 | 0.37 |
| PEP | 0.4 OD Nickelized polyethylene terephthalate | 0.58 | 0.24 |
| PEP | PIER | 0.74 | 0.26 |
| PIER | PIER | 0.40 | 0.15 |

TABLE IV

Example 3
Material 3 from Table I

| DISPERSION | CHARGE EXCHANGE ELECTRODES | $D_{MAX}$ | $D_{MIN}$ |
|---|---|---|---|
| PEP | 0.1 OD Cermet (Cr . SiO) Evaporated on polyethylene terephthalate | 0.43 | 0.22 |
| PEP | 0.4 OD Nickelized polyethylene terephthalate | 0.44 | 0.24 |
| PEP | PIER | 0.40 | 0.20 |
| PIER | PIER | 0.26 | 0.18 |

In the following Examples 4 through 25, image quality was determined visually with regard to Dmax, Dmin., speed and color saturation. Most of the materials were tested in both the PIER and PEP processes of migration imaging. In the case of PIER, the conductive layer and dark charge exchange layer are the same as previously described. In the case of PEP, the conductive layer consists of Cermet (Cr.SiO) coated on an estar film base. The results are described in Table V. In each case, the charge exchange electrode was negatively charged.

TABLE V

| EXAMPLE NUMBER | TABLE I MATERIAL | n | PEP IMAGE QUALITY | PIER IMAGE QUALITY |
| --- | --- | --- | --- | --- |
| 4 | 1 | 2 | Excellent | Very Good |
| 5 | 2 | 2 | Very Good | Very Good |
| 6 | 3 | 2 | Very Good | Very Good |
| 7 | 4 | 1 | Poor | Fair |
| 8 | 5 | 1 | No Image | Poor |
| 9 | 6 | 2 | Poor | Poor |
| 10 | 8 | 1 | Poor | No Image |
| 11 | 10 | 2 | Fair | Fair |
| 12 | 12 | 2 | Poor | Fair |
| 13 | 13 | 2 | Fair | Fair |
| 14 | 14 | 1 | Poor | Fair |
| 15 | 15 | 2 | Fair | Good |
| 16 | 16 | 1 | No Image | Poor |
| 17 | 17 | 2 | No Image | Poor |
| 18 | 18 | 2 | Poor | Poor |
| 19 | 19 | 2 | No Image | Poor |
| 20 | 20 | 2 | Very Good | Very Good |
| 21 | 21 | 2 | Fair | Fair |
| 22 | 22 | 2 | No Image | Fair |
| 23 | 23 | 2 | Very Good | — |
| 24 | 24 | 2 | Good | — |
| 25 | 25 | 2 | Very Weak | — |

The invention has been described in detail with particular reference to certain preferred embodiments thereof, but it will be understood that variations and modifications can be effected within the spirit and scope of the invention.

We claim:

1. A material having the following structure:

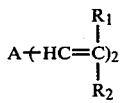

wherein

A represents phenylene, naphthylene, anthracenediyl and dibenzothiendiyl;

$R_1$ and $R_2$ both represent cyano or when taken together represent sufficient atoms to form a substituted or unsubstituted furanylidene and said substituents are selected from the group consisting of cyano, phenyl, nitrophenyl and oxo.

2. A material selected from the group consisting of:
5,5'-(9,10-anthracenediyldimethylidyne)bis[3-cyano-4-phenyl(5H)-furan-2-one]
5,5'-(9,10-anthracenediyldimethylidyne)bis[3,4-di(p-nitrophenyl)-(5H)-furan-2-one]
9,10-bis(dicyanoethenyl)anthracene
5,5'-(9,10-anthracenediyldimethylidyne)bis(1,3-diethyl-1,3,5-trihydro-pyrimidine-2,4,6-trione)
2,2'-(9,10-anthracenediyldimethylidyne)bis(indan-1,3-dione)
5,5'-(9,10-anthracenediyldimethylidyne)bis(N-ethyl-2-thioxothiazolidin-4-one)
5,5'-(9,10-anthracenediyldimethylidyne)bis(3-carbamoyl-4-phenyl-furan-2-one)
5-(9-anthracenylmethylidyne)-3-cyano-4-phenyl-furan-5-one
4,4'-(9,10-anthracenediyldimethylidyne)bis(3-phenyl-isoxazolin-5-one)
4-(9-anthracenylmethylidyne)-3-phenyl-isoxazolin-5-one
5,5'-(9,10-anthracenediyldimethylidyne)bis(2-thioxothiazolidin-4-one)
4,4'-(1,4-phenylenedimethylidyne)bis(3-carbamoyl-1-phenyl pyrazolin-5-one)
2,6-bis(dicyanoethenyl)naphthalene
5,5'-(2,6-naphthalenediyldimethylidyne)bis(3-cyano-4-phenylfuran-2-one)
2,6-bis[β-cyano-β-(p-cyanophenyl)ethenyl]naphthalene
5,5'-(dibenzothien-2,8-diyldimethylidyne)bis(3-cyano-4-phenyl-furan-2-one)
5,5'-(dibenzothien-2,8-diyldimethylidyne)bis[3,4-di(p-nitrophenyl)-furan-2-one] and
5,5'-(dibenzothien-2,8-diyldimethylidyne)bis(3-carbamoyl-4-phenyl-furan-2-one).

* * * * *